United States Patent [19]

Yamamoto et al.

[11] Patent Number: 4,608,369
[45] Date of Patent: Aug. 26, 1986

[54] TRITHIOPHOSPHORIC ACID ESTER AS A SOIL PESTICIDE

[75] Inventors: Haruyasu Yamamoto, Takarazuka; Takayuki Okabe, Nishinomiya, both of Japan

[73] Assignee: Sumitomo Chemical Company, Limited, Osaka, Japan

[21] Appl. No.: 666,324

[22] Filed: Oct. 31, 1984

[30] Foreign Application Priority Data

Nov. 4, 1983 [JP] Japan .................. 58-207786
Dec. 16, 1983 [JP] Japan .................. 58-238338

[51] Int. Cl.$^4$ .................. A01N 57/04; C07F 9/165
[52] U.S. Cl. .................. 514/144; 558/208
[58] Field of Search .................. 260/963; 514/144; 558/208

[56] References Cited

U.S. PATENT DOCUMENTS 3,112,244 11/1963 Goyette .................. 514/144
3,839,510 10/1974 Kudamatsu et al. .................. 260/963

FOREIGN PATENT DOCUMENTS 145230 6/1985 European Pat. Off. .
2232075 1/1973 Fed. Rep. of Germany .
2075508 10/1971 France .
83/00870 3/1983 World Int. Prop. O. .......... 260/963
485414 4/1970 Switzerland .

OTHER PUBLICATIONS

Chemical Abstracts, vol. 72, No. 17, 4/27/1970, p. 348, No. 90039h.
Chemical Abstracts, vol. 70, No. 9, 3/3/1969, p. 270, No. 37096g.

*Primary Examiner*—Anton H. Sutto
*Attorney, Agent, or Firm*—Stevens, Davis, Miller & Mosher

[57] ABSTRACT

A trithiophosphoric acid ester of the formula:

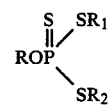

wherein R is lower alkyl group, and $R_1$ and $R_2$ are different from each other, $R_1$ is $C_1$-$C_4$ alkyl group and $R_2$ is isobutyl, sec-butyl or tert-butyl group, which is useful as a soil pesticidal composition for pests in soil.

5 Claims, No Drawings

TRITHIOPHOSPHORIC ACID ESTER AS A SOIL PESTICIDE

The present invention relates to a trithiophosphoric acid ester of the formula (hereinafter referred to as present compound):

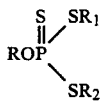  (I)

wherein $R_1$ is lower alkyl group, and $R_1$ and $R_2$ are different from each other, $R_1$ is $C_1$–$C_4$ alkyl group and $R_2$ is isobutyl, sec-butyl or tert-butyl group, its production and soil pesticidal compositions containing it as an active ingredient.

In the formula (I), the lower alkyl group means an alkyl group having not more than six carbon atoms.

That some kinds of trithiophosphoric acid ester, for example, O-ethyl S,S-di-sec-butyl trithiophosphate, O-ethyl S,S-di-isobutyl trithiophosphate, etc., can be used as an active ingredient for insecticides and nematocides, is described in U.S. Pat. No. 3,839,510. But, it may not always be said that these compounds are always satisfactory as an active ingredient for soil pesticides.

While, the present compound has a high controlling activity against pests living in soil and doing damage to paddy rice, vegetables, flowers and ornamental plants, lawn grasses, fruit trees, tea, mulberry and the like, and besides said compound gives no such phytotoxicity as to become a problem to these plants.

The present compound, therefore, can be used as an active ingredient for soil pesticidal compositions used for paddy field, plowland, orchard, pasture, tea garden, mulberry farm and the like.

The soil pest includes for example pests of Diabrotica genus such as western corn rootworm (*Diabrotica virgifera* Le Conte), northern corn rootworm (*Diabrotica longicornis* Say), southern corn rootworm (*Diabrotica undecimpunctata howardi* Barber), etc., pests of Anomala genus such as cupreous chafer (*Anomala cuprea* Hope), soybean beetle (*Anomala rufocuprea* Motschulsky), cherry chafer (*Anomala daimiana* Harlod), striated chafer (*Anomala testaceips* Motschulsky), etc., pests of Popillia genus such as Japanese beetle (*Popillia japonica* Newman), etc., pests of Aulacophora genus such as cucurbit leaf beetle (*Aulacophora femoralis* Motschulsky), etc., pests of Phyllotreta genus such as striped cabbage flea beetle (*Phyllotreta vittata* Fabricius), etc., pests of Melanotus genus such as sweetpotato wireworm (*Melanotus caudex* Lewis), etc., pests of Agriotes genus such as barley wireworm (*Agriotes fuscicollis* Miwa), etc., pests of Hylemya genus such as onion maggot (*Hylemya antiqua* Meigen), turnip maggot (*Hylemya floralis* Fallen), seed-corn maggot (*Hylemya platura* Meigen), etc., pests of Agrotis genus such as common cutworm (*Agrotis segetum* Denis et Schiffermüler), black cutworm (*Agrotis ipsilon* Hufnagel), etc., pests of Gryllotalpa genus such as African mole cricket (*Gryllotalpa africana* Palisot de Beauvois), etc., pests of Lissorhoptrus genus such as ricewater weevil (*Lissorhoptrus oryzophilus* Kuschel), etc., pests of Pratylenchus genus such as Cobb root-lesion nematode (*Pratylenchus penetrans* Cobb), walnut root-lesion nematode (*Pratylenchus vulnus* Allen et Jensen), coffee root-lesion nematode (*Pratylenchus coffeae* Zimmermann), etc., pests of Heterodera genus such as soybean cyst nematode (*Heterodera glycines* Ichinohe), etc., pests of Meloidogyne genus such as northern root-knot nematode (*Meloidogyne hapla* Chitwood), cotoon root-knot nematode (*Meloidogyne incognita* var. *acrita* Chitwood), Javanese root-knot nematode (*Meloidogyne javanica* Treub), peanut root-knot nematode (*Meloidogyne arenaria* Neal), etc., pests of Aphelenchoides genus such as rice whitetip nematode (*Aphelenchoides besseyi* Christie) and the like.

The present compound can be produced by reacting a dithiolphosphoric acid ester of the formula:

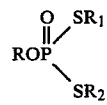  (II)

wherein R, $R_1$ and $R_2$ are each as defined above, with a 1,3-dithia-2,4-diphosphethane-2,4-disulfide of the formula:

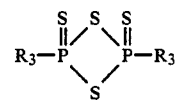  (III)

wherein $R_3$ is lower alkyl, phenyl or thiophene group or phenyl group substituted with halogen atom, lower alkyl or lower alkoxyl group.

The reaction is generally carried out in a solvent not disturbing its progress such as hydrocarbons (e.g. n-hexane, benzene, toluene, xylene), ethers (e.g. tetrahydrofuran, dioxane), halogenated hydrocarbons (e.g. chlorobenzene, dichlorobenzene) and the like.

As to the amount of reagent used for reaction, 1,3-dithia-2,4-diphosphethane-2,4-disulfide (III) of at least 0.5 mole is used based on 1 mole of a dithiophosphoric acid ester (II). The reaction temperature is about 80° to about 120° C., and the reaction time is about 30 minutes to about 10 hours.

After completion of the reaction, the reaction product is purified by chromatography, distillation, etc. if necessary.

Production examples for the present compound will be shown.

PRODUCTION EXAMPLE

To a solution of 2.7 g of O-ethyl S-sec-butyl S-tert-butyl phosphorodithiolate in 50 ml of toluene was added 2.1 g of 2,4-bis(4-methoxyphenyl)-1,3-dithia-2,4-diphosphethane-2,4-disulfide, and the mixture was refluxed for 1 hour with stirring. Toluene was removed by evaporation under reduced pressure, and a pale yellow oily product obtained as a residue was purified by column chromatography on silica gel to obtain 2.1 g of a colorless and oily O-ethyl S-sec-butyl S-tert-butyl phosphorotrithioate.

$n_D^{29}$ 1.5361

The present compounds which can be produced by this method will be shown in Table 1.

TABLE 1

Trithiophosphoric acid ester of the formula:

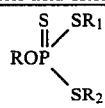

| Compound No. | R | $R_1$ | $R_2$ | Physical constant |
|---|---|---|---|---|
| (1) | $C_2H_5$ | sec-$C_4H_9$ | tert-$C_4H_9$ | $n_D^{29}$ 1.5361 |
| (2) | " | iso-$C_4H_9$ | " | $n_D^{29}$ 1.5326 |
| (3) | " | n-$C_4H_9$ | " | $n_D^{21}$ 1.5383 |
| (4) | " | iso-$C_3H_7$ | " | $n_D^{21}$ 1.5406 |
| (5) | " | n-$C_3H_7$ | " | $n_D^{29}$ 1.5408 |
| (6) | " | $C_2H_5$ | " | $n_D^{26}$ 1.5473 |
| (7) | " | $CH_3$ | " | $n_D^{26}$ 1.5524 |
| (8) | $CH_3$ | sec-$C_4H_9$ | " | $n_D^{28}$ 1.5440 |
| (9) | " | iso-$C_4H_9$ | " | $n_D^{28}$ 1.5425 |
| (10) | " | n-$C_4H_9$ | " | $n_D^{21}$ 1.5438 |
| (11) | " | iso-$C_3H_7$ | " | $n_D^{21}$ 1.5470 |
| (12) | " | n-$C_3H_7$ | " | $n_D^{22}$ 1.5458 |
| (13) | " | $C_2H_5$ | " | $n_D^{22}$ 1.5528 |
| (14) | " | $CH_3$ | " | $n_D^{21}$ 1.5562 |
| (15) | $C_2H_5$ | iso-$C_4H_9$ | sec-$C_4H_9$ | $n_D^{28}$ 1.5387 |
| (16) | " | n-$C_4H_9$ | " | $n_D^{25}$ 1.5315 |
| (17) | " | iso-$C_3H_7$ | " | $n_D^{24}$ 1.5329 |
| (18) | " | n-$C_3H_7$ | " | $n_D^{26}$ 1.5360 |
| (19) | " | $C_2H_5$ | " | $n_D^{28}$ 1.5420 |
| (20) | " | $CH_3$ | " | $n_D^{28}$ 1.5645 |
| (21) | $CH_3$ | iso-$C_4H_9$ | " | $n_D^{21}$ 1.5436 |
| (22) | " | n-$C_4H_9$ | " | $n_D^{21}$ 1.5449 |
| (23) | " | iso-$C_3H_7$ | " | $n_D^{21}$ 1.5457 |
| (24) | " | n-$C_3H_7$ | " | $n_D^{22}$ 1.5460 |
| (25) | " | $C_2H_5$ | " | $n_D^{22}$ 1.5479 |
| (26) | " | $CH_3$ | " | $n_D^{22}$ 1.5509 |
| (27) | $C_2H_5$ | n-$C_4H_9$ | iso-$C_4H_9$ | $n_D^{25}$ 1.5328 |
| (28) | " | iso-$C_3H_7$ | " | $n_D^{28}$ 1.5300 |
| (29) | " | n-$C_3H_7$ | " | $n_D^{26}$ 1.5410 |
| (30) | " | $C_2H_5$ | " | $n_D^{22}$ 1.5467 |
| (31) | " | $CH_3$ | " | $n_D^{22}$ 1.5500 |
| (32) | $CH_3$ | n-$C_4H_9$ | " | $n_D^{21}$ 1.5468 |
| (33) | " | iso-$C_3H_7$ | " | $n_D^{29}$ 1.5370 |
| (34) | " | n-$C_3H_7$ | " | $n_D^{22}$ 1.5500 |
| (35) | " | $C_2H_5$ | " | $n_D^{23}$ 1.5440 |
| (36) | " | $CH_3$ | " | $n_D^{22}$ 1.5600 |

When the present compounds are used as an active ingredient for soil pesticidal compositions, they are generally formulated into oil sprays, emulsifiable concentrates, wettable powders, granules, dusts, aerosols, etc., by mixing with an inert carrier such as solid, liquid or gaseous carrier and if necessary, adding auxiliaries for formulation such as surface active agents and others.

These compositions contain 0.1 to 99.9% by weight, preferably 1 to 80% by weight of the present compound as an active ingredient.

The solid carrier includes for example fine powders or granules of clays (e.g. kaolin clay, attapulgite clay, diatomaceous earth, synthetic hydrated silicon dioxide, Fubasami clay, bentonite, terra abla), talcs, other inorganic minerals (e.g. sericite, quartz powder, sulfur powder, activated carbon, calcium carbonate, hydrated silica), chemical fertilizers (e.g. ammonium sulfate, ammonium phosphate, ammonium nitrate, urea, ammonium chloride) and the like. The liquid carrier includes for example water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. n-hexane, cyclohexane, kerosene, petroleum ether), esters (e.g. ethyl acetate, butyl acetate), nitriles (e.g. acetonitrile, isobutyronitrile), ethers (e.g. dioxane, diisopropyl ether), acid amides (e.g. dimethylformamide, dimethylacetamide), halogenated hydrocarbons (e.g. dichloroethane, trichloroethylene, carbon tetrachloride) and the like. The gaseous carrier, i.e. propellant, includes for example freon gas, butane gas, carbon dioxide gas and the like.

The surface active agent includes for example alkyl sulfates, alkylarylsulfonates, alkylsulfonates, alkyl aryl ethers and their polyoxyethylenized products, polyethylene glycol ethers, polyhydric alcohol esters, sugar alcohol derivatives and the like.

The fixing agent and dispersing agent include for example casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids) and the like. The stabilizer includes for example PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surface active agents, fatty acids and their esters, and the like.

These compositions may be used, as such or as aqueous dilute liquors, by spraying or scattering onto soil surface and if necessary, mixing with the soil after spraying or scattering, or drenching soil. Sometimes, they may be used in foliar spraying. Also, they may be used in mixture with other insecticides, acaricides, nematocides, fungicides, seed disinfectants, fertilizers or soil improvers, or may be used at the same time together with these chemicals without mixing.

Formulation examples for the present compound will be shown. Hereupon, all parts are by weight.

FORMULATION EXAMPLE 1

Emulsifiable concentrate

40 Parts of each of the present compounds (1) to (36) is dissolved in 50 parts of xylene, and 10 parts of Sorpol SM-200, an emulsifier, (mixture of polyoxyethylene alkylaryl ether, etc., and dodecylbenzenesulfonic acid; a registered trade mark of Toho Kagaku Co.) is added thereto. The mixture is then well mixed by stirring to obtain a 40% emulsifiable concentrate of each compound.

FORMULATION EXAMPLE 2

Wettable powder

To 40 parts of each of the present compounds (1) to (36) is added 5 parts of Sorpol SM-200, and after thorough mixing, 20 parts of Carplex #80 (synthetic hydrated silicon dioxide fine powder; a registered trade mark of Shionogi Seiyaku Co.) and 35 parts of 300-mesh diatomaceous earth are added thereto. The mixture is then mixed by stirring on a juice mixer to obtain a 40% wettable powder of each compound.

FORMULATION EXAMPLE 3

Granule

To 5 parts of each of the present compounds (1) to (36) are added 5 parts of Toyolignin CT (ligninsulfonate; a registered trade mark of Toyo Spinning Co.) and 90 parts of GSM clay (quartz powder; a registered trade mark of Zieklite Mining Co.), and the mixture is well mixed by stirring on a mortar. Thereafter, to the mixture is added water corresponding to 10% thereof, and the resulting mixture is further stirred, granulated on a granulator and air-dried to obtain a 5% granule of each compound.

FORMULATION EXAMPLE 4

Dust

5 Parts of each of the present compounds (1) to (36) is dissolved in 20 parts of acetone, and 3 parts of Carplex #80, 0.3 part of PAP and 91.7 parts of 300-mesh talc are added thereto. The resulting mixture is mixed by stirring on a juice mixer, and acetone is removed by evaporation to obtain a 5% dust of each compound.

FORMULATION EXAMPLE 5

Oil spray

20 Parts of each of the present compounds (1) to (36) is dissolved in 80 parts of kerosene to obtain a 20% oil spray of each compound.

FORMULATION EXAMPLE 6

Granule

15 Parts of each of the present compounds (1) to (36) is dissolved in 10 parts of diethylene glycol, and the resulting solution is well mixed with 75 parts of Attapulgus clay 25/50 mesh (attapulgite clay produced by Engelhard Co.) while spraying the solution onto the stirred clay. A 15% granule of each compound is thus obtained.

When the present compounds are used as an active ingredient for soil pesticidal compositions, the dosage rate is generally 10 to 1000 g/10 ares, preferably 50 to 500 g/10 ares, and the application concentration is 0.01 to 30% when the emulsifiable concentrate, wettable powder or the like is diluted with water.

These dosage rate and application concentration vary with the form of preparation, application time, application scene, application method, kind of soil pest, degree of damage and the like, so that they may be increased or decreased independently of the foregoing ranges.

The controlling activity on soil pests of the present compounds will be shown with reference to the following test examples. Every test example was carried out according to a three-replication test. Of the test compounds, the present compounds are shown by Compound No. in Table 1 and compounds used as a control are shown by Compound symbol in Table 2.

TABLE 2

| Compound symbol | Chemical structure | Remark |
| --- | --- | --- |
| (A) | n-$C_3H_7S$, $C_2H_5O$ — P(=O) — S—n-$C_3H_7$ | Ethoprophos |
| (B) | sec-$C_4H_9S$, $C_2H_5O$ — P(=S) — S—sec-$C_4H_9$ | Compound described in U.S. Pat. No. 3839510. |
| (C) | iso-$C_4H_9S$, $C_2H_5O$ — P(=S) — S—iso-$C_4H_9$ | Compound described in U.S. Pat. No. 3839510. |

TEST EXAMPLE 1

The emulsifiable concentrate of each test compound formulated according to Formulation example 1 was diluted with water, and 5 ml of the resulting aqueous dilute liquor was mixed with 50 g of soil (16 mesh) to make the concentration of active ingredient in soil 1 ppm. The soil was then placed in a polyethylene cup of 5.6 cm in diameter and 5.8 cm high, and two pieces of corn having roots of 2 to 3 cm long were planted. At the same time, ten third instar larvae of southern corn rootworm (*Diabrotica undecimpunctata howardi* BARBER) were liberated in the cup. Two days after liberation, the number of the dead and alive of the larvae was examined to obtain mortality (%). The result is shown in Table 3.

TABLE 3

| Test compound | Mortality (%) |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (21) | 100 |
| (22) | 100 |
| (23) | 100 |
| (24) | 100 |
| (25) | 100 |
| (26) | 100 |
| (27) | 100 |
| (28) | 100 |
| (29) | 100 |
| (30) | 100 |
| (31) | 100 |
| (32) | 100 |
| (33) | 100 |
| (34) | 100 |
| (35) | 100 |
| (36) | 100 |
| No treatment | 0 |

TEST EXAMPLE 2

The emulsifiable concentrate of each test compound formulated according to Formulation example 1 was diluted with water, and 50 ml of the resulting aqueous dilute liquor was mixed with 500 g of soil (16 mesh) to make the concentrations of active ingredient in soil 0.5 and 0.25 ppm. The soil was then placed in a polyethylene cup of 12 cm in diameter and 8 cm high, and four pieces of corn having a bud of 5 to 6 cm long were planted. At the same time, twenty third instar larvae of southern corn rootworm (*Diabrotica undecimpunctata howardi* BARBER) were liberated in the cup. Two days after liberation, the number of the dead and alive of the larvae was examined to obtain mortality (%). The result is shown in Table 4.

TABLE 4

| Test compound | Mortality (%) | |
| --- | --- | --- |
| | 0.5 ppm | 0.25 ppm |
| (2) | 90 | 20 |
| (4) | 95 | 5 |

TABLE 4-continued

| Test compound | Mortality (%) | |
|---|---|---|
| | 0.5 ppm | 0.25 ppm |
| (5) | 100 | 50 |
| (17) | 90 | 10 |
| (31) | 100 | 80 |
| (33) | 100 | 95 |
| (36) | 100 | 100 |
| (A) | 50 | 0 |
| (B) | 0 | 0 |
| (C) | 0 | 0 |

TEST EXAMPLE 3

The emulsifiable concentrate of each test compound formulated according to Formulation example 1 was diluted with water, and 20 ml of the resulting aqueous dilute liquor was mixed with 500 g of soil to make the concentration of active ingredient in soil 1 ppm. The soil was then placed in a polyethylene cup of 12 cm in diameter and 8 cm high, and a piece of cut carrot was buried as bait. At the same time, four third instar larvae of cupreous chafer (*Anomala cuprea* Hope) were liberated in the cup. Seven days after liberation, the number of the dead and alive of the larvae was examined to obtain mortality (%). The result is shown in Table 5.

TABLE 5

| Test compound | Mortality (%) |
|---|---|
| (2) | 100 |
| (28) | 80 |
| (A) | 60 |
| No treatment | 0 |

What is claimed is:

1. A trithiophosphoric acid ester of the formula:

$$RO-P(=S)(SR_1)(SR_2)$$

wherein R is lower alkyl, $R_1$ is methyl and $R_2$ is isobutyl.

2. The trithiophosphoric acid ester according to claim 1, wherein R is ethyl.

3. The trithiophosphoric acid ester according to claim 1, wherein R is methyl.

4. A method for controlling soil pests which comprises applying a pesticidally effective amount of the trithiophosphoric acid ester according to claim 1 to the soil pests.

5. A soil pesticidal composition which comprises a pesticidally effective amount of the trithiophosphoric acid ester according to claim 1 as an active ingredient and an inert carrier.

* * * * *